United States Patent
Sohn et al.

(10) Patent No.: US 7,671,272 B2
(45) Date of Patent: Mar. 2, 2010

(54) HOLE TRANSPORTING MATERIAL AND SOLID ELECTROLYTE AND PHOTOVOLTAIC DEVICE USING SAME

(75) Inventors: Byung Hee Sohn, Yongin-Si (KR); Sang Cheol Park, Seoul (KR); Jung Gyu Nam, Yongin-Si (KR)

(73) Assignee: Samsung Electronics Co., Ltd. (KR)

( * ) Notice: Subject to any disclaimer, the term of this patent is extended or adjusted under 35 U.S.C. 154(b) by 939 days.

(21) Appl. No.: 11/447,322

(22) Filed: Jun. 6, 2006

(65) Prior Publication Data

US 2007/0085051 A1 Apr. 19, 2007

(30) Foreign Application Priority Data

Oct. 18, 2005 (KR) .................... 10-2005-0097993

(51) Int. Cl.
*H01L 31/00* (2006.01)
(52) U.S. Cl. .................... 136/263; 429/104; 429/111; 429/188; 313/483; 313/504; 313/506; 428/690; 548/126; 528/397; 528/422; 528/423; 257/E51.028; 257/E51.036

(58) Field of Classification Search ................. 136/263; 429/104, 111, 188; 313/483, 504, 506; 428/690; 548/126; 528/397, 422, 423; 257/E51.028, 257/E51.036
See application file for complete search history.

(56) References Cited

U.S. PATENT DOCUMENTS

2004/0265587 A1* 12/2004 Koyanagi et al. ........... 428/398
2006/0014092 A1* 1/2006 Nukada et al. ................ 430/60

FOREIGN PATENT DOCUMENTS

WO    WO 2006/015862    *    2/2006

* cited by examiner

*Primary Examiner*—Basia Ridley
*Assistant Examiner*—Thanh-Truc Trinh
(74) *Attorney, Agent, or Firm*—Cantor Colburn LLP

(57) ABSTRACT

Disclosed herein is a material, and a solid electrolyte and a photovoltaic device using the same. When the material is used as a hole transporting layer material of the photovoltaic device, the reduction of an electrolytic layer resulting from leakage or volatilization of an electrolytic solution is prevented, thus the battery characteristics, long-term stability, and reliability of the photovoltaic device are improved.

12 Claims, 3 Drawing Sheets

HOLE TRANSPORTING MATERIAL AND SOLID ELECTROLYTE AND PHOTOVOLTAIC DEVICE USING SAME

This non-provisional application claims priority under 35 U.S.C. §119(a) to Korean Patent Application No. 2005-97933 filed on Oct. 18, 2005, the entire contents of which are hereby incorporated by reference.

BACKGROUND OF THE INVENTION

1. Field of the Invention

The present invention relates to a material, a solid electrolyte and a photovoltaic device using the same. More particularly, the present invention pertains to a novel hole transporting material that has advantageous electrically conductive properties so that it can be used as a solid electrolyte in a photovoltaic device.

2. Description of the Related Art

A solar cell is a photovoltaic device for converting sunlight into electrical energy. Their ability to convert sunlight into electrical energy is unlimited. These are also environmentally friendly and hence their popularity has been growing over time. In particular, the use of photovoltaic cells in portable information devices, such as portable computers, portable phones, and personal digital assistants, renders these portable information devices versatile.

Mono- and poly-silicon solar cells have been frequently used in a variety of applications. However, the silicon solar cell is disadvantageous since the production costs of silicon are high, the raw materials are expensive, and because it is difficult to improve the conversion efficiency of solar energy into electric energy.

Accordingly, interest in solar cells that are capable of being produced inexpensively from organic materials has increased. In particular, dye-sensitized solar cells that have low production costs are of interest. The dye-sensitized solar cell is a photo electrochemical solar cell that comprises a porous semiconductor layer including nanoparticles attached to a transparent electrode, a light absorption layer including a dye adsorbed on the semiconductor layer, and an electrolytic solution for oxidation and reduction charged between the two electrodes. The dye-sensitized solar cell is advantageous in that the photoelectric conversion efficiency thereof is high and the production cost is low.

However, since the dye-sensitized solar cell is a wet-type cell that comprises a liquid electrolyte, its photoelectric conversion efficiency is reduced over time due to leakage of the electrolytic solution or volatilization of the electrolytic solution. Thus the reliability and long-term stability are reduced.

In order to avoid the problems of the wet-type solar cell, many studies have been conducted into solar cells that employ a solid polymer electrolyte used as a hole transporting material instead of the electrolytic solution.

SUMMARY OF THE INVENTION

Accordingly, the present invention provides a material that has conductive properties and excellent reliability.

The present invention further provides an electrolyte having excellent reliability and long-term stability. It also discloses a photovoltaic device comprising the electrolyte.

In another embodiment, the present invention provides a material shown in Formula 1.

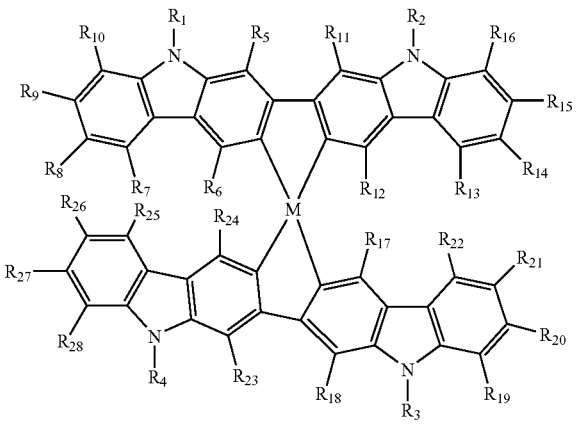

Formula 1

In Formula 1, $R_1$ to $R_{28}$ are the same as or different from each other, and are independently selected from the group consisting of hydrogen, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C5-C30 heteroaryl group, a substituted or unsubstituted C5-C30 heteroarylalkyl group, a substituted or unsubstituted C5-C30 heteroaryloxy group, a substituted or unsubstituted C5-C20 cycloalkyl group, and a substituted or unsubstituted C5-C30 heterocycloalkyl group, and M is C or Si.

Another embodiment of the present invention provides an electrolyte comprising the novel hole transporting material of the present invention.

The electrolyte of the present invention is a solid electrolyte, and may comprise the material of Formula 1, a second hole transporting material, such as triphenylmethane, carbazole, N,N'-diphenyl'-N,N'-bis(3-methylphenyl)-1,1'biphenyl)-4,4'diamine (TPD), or a combination thereof along with an additive.

Still another aspect of the present invention provides an electronic device that comprises a hole transporting layer including the material of Formula 1. The electronic device may be a photovoltaic device or an electroluminescent device.

BRIEF DESCRIPTION OF THE DRAWINGS

The above features and advantages of the present invention will be more clearly understood from the following detailed description taken in conjunction with the accompanying drawings, in which.

DESCRIPTION OF THE PREFERRED EMBODIMENTS

Hereinafter, a detailed description will be given of the present invention, referring to the accompanying drawings.

The material of the present invention has the structure shown in the following Formula 1.

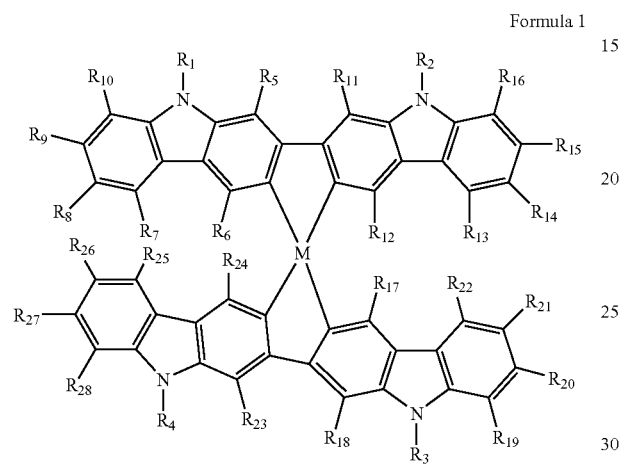

Formula 1

In Formula 1, $R_1$ to $R_{28}$ are the same as or different from each other, and are independently selected from the group consisting of hydrogen, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C5-C30 heteroaryl group, a substituted or unsubstituted C5-C30 heteroarylalkyl group, a substituted or unsubstituted C5-C30 heteroaryloxy group, a substituted or unsubstituted C5-C20 cycloalkyl group, and a substituted or unsubstituted C5-C30 heterocycloalkyl group. M is C or Si.

Figure 1:
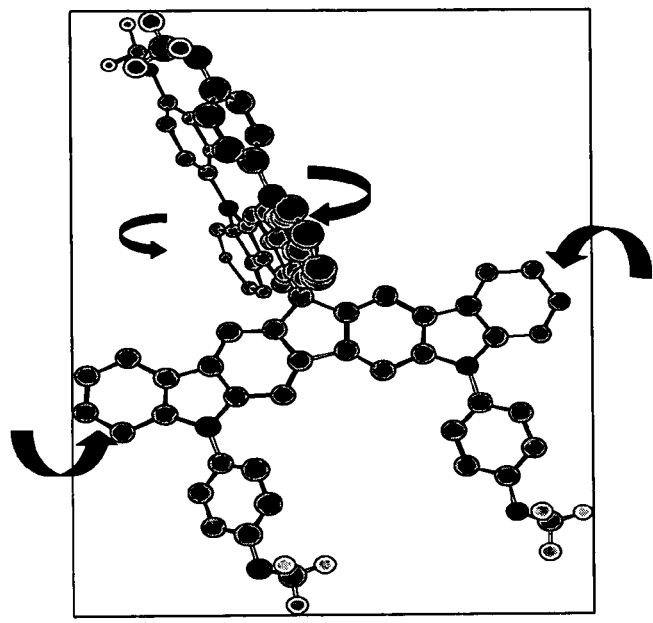
FIG. 1 illustrates the morphology of a material of the present invention.

FIG. 1 illustrates the morphology of the material of the present invention. As shown in FIG. 1, in the material of the present invention, a hole transporting moiety is a spiro type, in which two ring systems are connected through one tetravalent atom so as to form a three-dimensional antenna in space. The hole transporting material receives holes from dye cations and, since the hole transport mobility of the materials is sufficiently high, it efficiently transfers the hole.

The hole transporting material of the present invention may have a symmetrical or asymmetrical structure. In general, the hole transporting efficiency is increased when the structure is symmetrical. When R1 and R2, and R4 and R3 are identical substituent groups in Formula 1, the structure is symmetrical. When R1 and R2, and R4 and R3 are different substituent groups in Formula 1, then the structure is asymmetrical.

A preferred example of the material of the present invention has the structure shown in the following Formula 2.

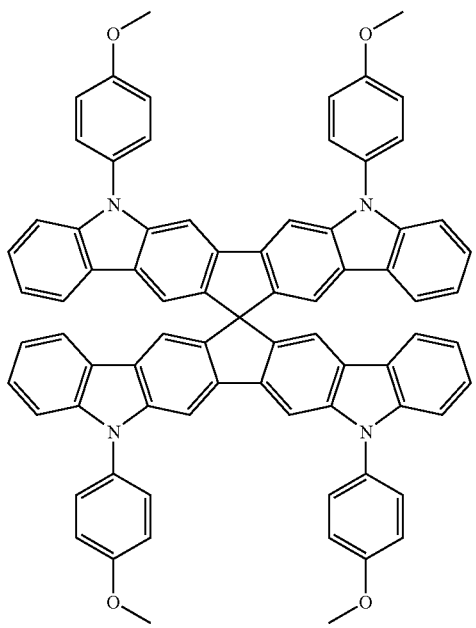

Formula 2

The material of the present invention may be dissolved in an organic solvent or in an inorganic solvent. Suitable examples of organic solvents include acetonitrile, ethylene carbonate, propylene carbonate, chloroform, benzene, chlorobenzene, cyclohexane, toluene, tetrahydrofuran, anisole, cresol, xylene, hexane and a combination comprising at least one of the foregoing solvents.

The material may be used as an electrolyte in a photovoltaic device or the like. The electrolyte containing the material may be a solid electrolyte or a gel-type electrolyte. The gel-type electrolyte may comprise an electrolytic composition comprising a solvent and a crosslinked matrix. The solid electrolyte may also comprise a crosslinked matrix. Since the electrolyte having the above-mentioned constitution includes a gel-type electrolyte or a complete solid-type electrolyte, the deterioration of properties resulting from leakage or volatilization of an electrolytic solution does not occur, and thus the electrolyte is highly reliable.

When it is used as the electrolyte, the hole transporting material of Formula 1 may be used along with a second hole transporting material or other additives. Any hole transporting material may be used as the second hole transporting material, without any limitations, as long as it is capable of performing a hole transporting function. Examples of other hole transporting materials that may be used in combination with the hole transporting material of Formula 1 are triphenylmethane, carbazole, N,N'-diphenyl'-N,N'-bis(3-methylphenyl)-1,1'biphenyl)-4,4'diamine (TPD), 2,2',7,7'-tetrakis-(N,N-di-methoxyphenylamine)-9,9'-spirobifluorene, and a combination comprising at least one of the foregoing hole transporting materials.

Another aspect of the present invention relates to an electronic device using the above-mentioned material. The material of the present invention may be used as a hole transporting layer material in a photovoltaic device or in an electroluminescent device.

Figure 2:
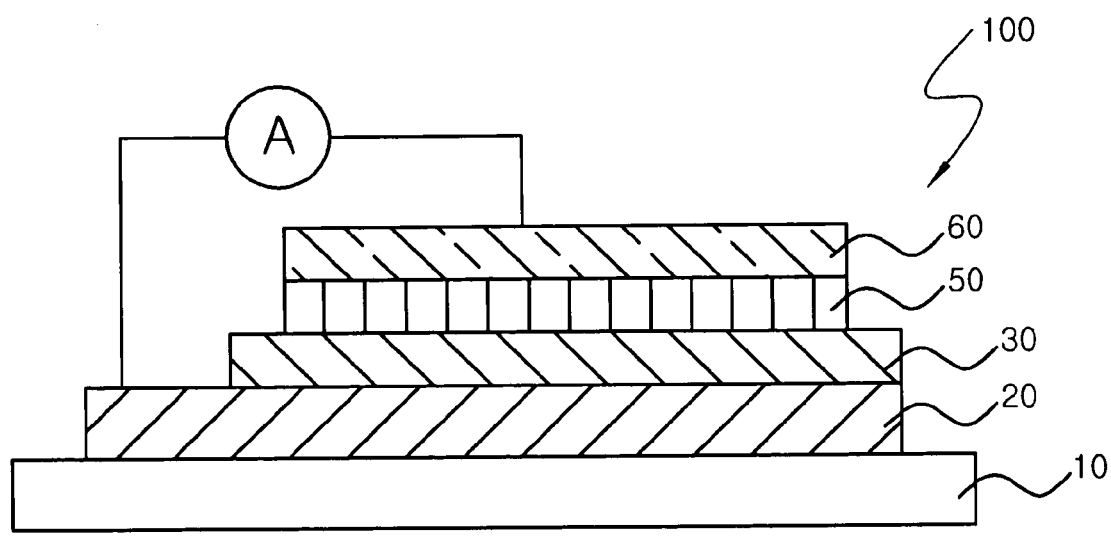
FIG. 2 is a sectional view of a photovoltaic device including the novel hole transporting material of the present invention.

FIG. 2 is a schematic sectional view of a dye-sensitized solar cell which is a photovoltaic device having the hole transporting material of the present invention. In FIG. 2, the dye-sensitized solar cell 100 comprises a transparent electrode 20. The transparent electrode 20 comprises an electrically conductive material that is applied to a substrate 10, a light absorption layer 30 which is formed on the transparent electrode 20 and includes a metal oxide layer having a dye adsorbed on a surface thereof, a counter electrode 60 facing the transparent electrode 20, and a hole transporting layer 50 interposed between the transparent electrode 20 and the counter electrode 60.

In the photovoltaic device of the present invention, the transparent electrode 20 is formed by applying the electrically conductive material on the substrate. The substrate is not limited as long as it is transparent, and may be exemplified by a transparent inorganic substrate, such as quartz or glass, or a transparent plastic substrate, such as polyethylene terephthalate (PET), polyethylene naphthalate (PEN), polycarbonate, polystyrene, polypropylene, polyimides, polyetherimides, or the like, or a combination comprising at least one of the foregoing materials.

The electrically conductive material applied on the substrate may be exemplified by indium tin oxide (ITO), fluorine-doped tin oxide (FTO), $ZnO-Ga_2O_3$, $ZnO-Al_2O_3$, $SnO_2-Sb_2O_3$, or the like, or a combination comprising at least one of the foregoing materials.

In the photovoltaic device of the present invention, the light absorption layer 30 comprises the metal oxide layer and the dye adsorbed on a surface of the metal oxide layer. It is necessary that the light absorption layer 30 absorbs as much light energy as possible in order to assure high efficiency. In order to attain a high efficiency, it is desirable for the surface to high a high surface area. This is generally accomplished by utilizing porous metal oxides and absorbing a dye thereon.

In the present invention, for example, the metal oxide layer may be made of one or more metal oxides selected from the group consisting of titanium oxide, niobium oxide, hafnium oxide, indium oxide, tin oxide, and zinc oxide. The metal oxide may be used alone or in a mixture including two or more. The metal oxide is preferably exemplified by $TiO_2$, $SnO_2$, $ZnO$, $WO_3$, $Nb_2O_5$, or $TiSrO_3$, and, more preferably anatase-type $TiO_2$.

With respect to the metal oxide constituting the light absorption layer 30, it is preferable that the dye adsorbed on the surface thereof absorb as much light as possible and that the surface area be enlarged so as to improve adsorption of light to the hole transporting layer. Accordingly, it is preferable that the metal oxide of the light absorption layer 30 has a nanostructure, such as a nanotube, a nanowire, a nanobelt, or a nanoparticle.

The particle sizes of particles that form the metal oxide layer are not limited. In one embodiment, it is generally desirable for the metal oxide to have an average particle size of about 1 to about 200 nm. In another embodiment, it is desirable for the metal oxide particles to have an average particle size of about 5 to about 100 nm. Furthermore, it is possible to use mixtures of two or more metal oxides, each metal oxide having different particle sizes so as to scatter incident light and improve quantum efficiency.

Any dye may be used without limitation, as long as the dye is used in solar cells. In one embodiment, the dye is a ruthenium complex. It is generally desirable for the dye to display electric charge separation and as well as be photosensitive. In addition to the ruthenium complex, other dyes that can be used are a xanthine-based dye, such as rhodamine B, rose bengal, eosin, or erythrosine; a cyanine-based dye, such as quinocyanine or cryptocyanine; a basic dye, such as phenosafranine, carby blue, thiosine, or methylene blue; a porphyrin-based compound, such as chlorophyll, zinc porphyrin, or magnesium porphyrin; an azo dye, a phthalocyanine compound, a complex, such as ruthenium trisbipyridyl, an anthraquinone-based dye, or a polycyclic quinone-based dye. They may be used alone or in a mixture including two or more.

In the photovoltaic device of the present invention, any conductive material may be used to produce the counter electrode 60, and it is possible to use an insulating material if an electrically conductive layer is formed on the side thereof that faces the transparent electrode. However, it is preferable to use an electrochemically stable material as an electrode. In general, it is preferable to use platinum, gold, carbon, carbon nanotubes (CNT), or the like, or a combination comprising at least one of the foregoing materials.

Additionally, it is preferable that the side facing the transparent electrode has a microstructure and a large surface area in order to improve a redox catalytic effect. For example, it is preferable to have a platinum layer coated with carbon black or carbon nanotubes on the side facing the transparent electrodes. This arrangement permits the surface facing the transparent electrode to have a high surface area.

The photovoltaic device is operated as described below. A dye adsorbed on the surface of the metal oxide layer absorbs light that penetrates through the counter electrode 60 and is incident on the light absorption layer 30. The dye absorbs light and transfers electrons from a ground state to an excited state thereby forming a pair of electron-holes in the process. The excited electron is injected into a conductive band of the metal oxide and then moved to electrodes to generate an electrical current. If the electron that is photo-excited in the dye moves to the conductive band of the metal oxide, the dye losing the electrons receives compensatory electrons from the material of the hole transporting layer 50 and is thereby restored to its original ground state.

The photovoltaic device of the present invention may be produced through the following procedure. First, a transparent electrode on which a conductive material is applied is prepared, and a semiconductor layer of a metal oxide is formed on a side of the transparent electrode.

The process of producing a film of a metal oxide layer is not limited to any particular process, but it is preferable to use a process comprising wet coating of the metal oxide. Such a process produces a film or the metal oxide layer that has good physical properties. The process is also convenient, and has a low production cost.

In one embodiment, it is preferable to use a process that comprises preparing a paste in which metal oxide powder is uniformly dispersed in a proper solvent and coating a substrate with the paste to form a transparent conductive film. In connection with this, the coating method may be exemplified by a typical coating method, for example, spraying, spin coating, dipping, printing, doctor blading, sputtering, electrophoresis, or a combination comprising at least one of the foregoing processes.

When the metal oxide layer is formed drying and sintering steps are conducted. The drying step may be conducted at about 50 to about 100° C. and the sintering step may be conducted at about 400 to about 500° C.

Next, the metal oxide layer is dipped in a solution containing a photosensitive dye for 12 hours or more to adsorb the dye on the surface of the metal oxide. Examples of the solvent used in the solution containing the photosensitive dye include tertiary butyl alcohol, acetonitrile, or mixtures thereof.

When the photovoltaic device is produced according to the method of the present invention, an electrolyte which includes a material of the present invention alone or in conjunction with a second hole transporting material (a second material) or an additive, such as a binder, is prepared to form a hole transporting layer on the semiconductor layer through a spin coating method or the like.

In the present invention, the method of forming the hole transporting layer 50 is not limited to any particular process. Any method that increases adhesion between the metal oxide of the metal oxide layer or the counter electrode 60 and the hole transporting material can be used. It may be exemplified by spin coating, dipping, spraying, roll coating, blade coating, gravure coating, screen printing, doctor blading, electrophoresis, or a combination comprising at least one of the foregoing processes.

The material of the present invention may be used as a hole transporting material of an electroluminescent device as well as a dye-sensitized photovoltaic device. Particularly, the hole transporting material of the present invention is useful for producing a flexible photovoltaic device or a flexible organic electroluminescent device.

A better understanding of the present invention may be obtained in light of the following examples which are set forth to illustrate, but are not to be construed to limit the present invention.

Synthesis Example of Hole Transporting Material

A hole transporting material (compound 7 in the following Reaction Equation 1) of the present invention shown in Formula 2 was synthesized according to a reaction scheme of the following Reaction Equation 1.

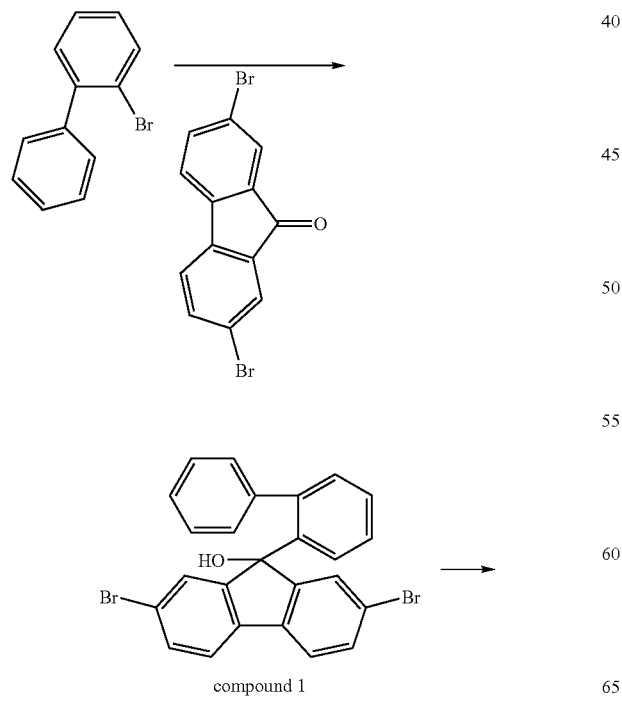

Reaction Equation 1 compound 1

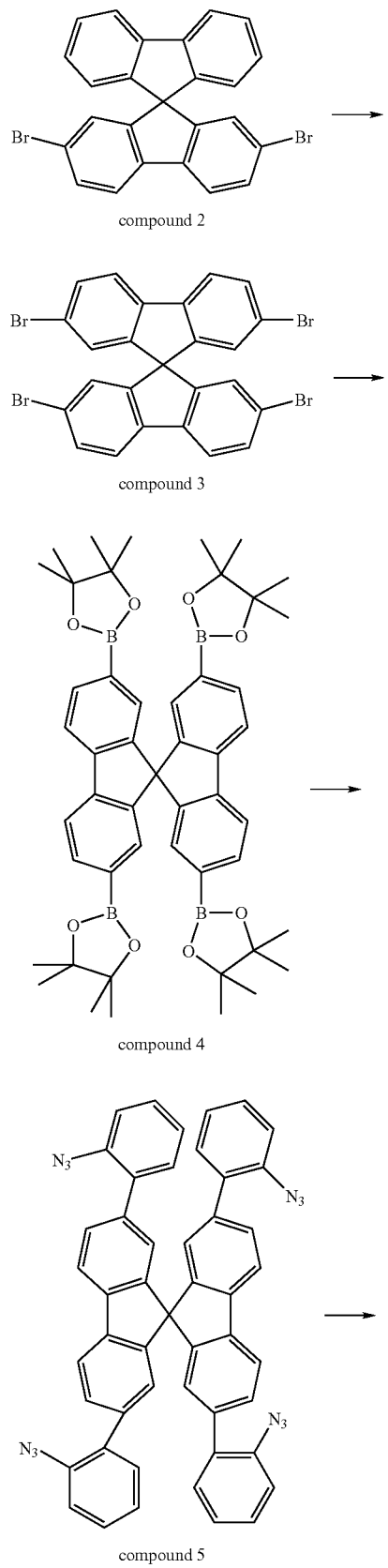

-continued compound 2 compound 3 compound 4 compound 5

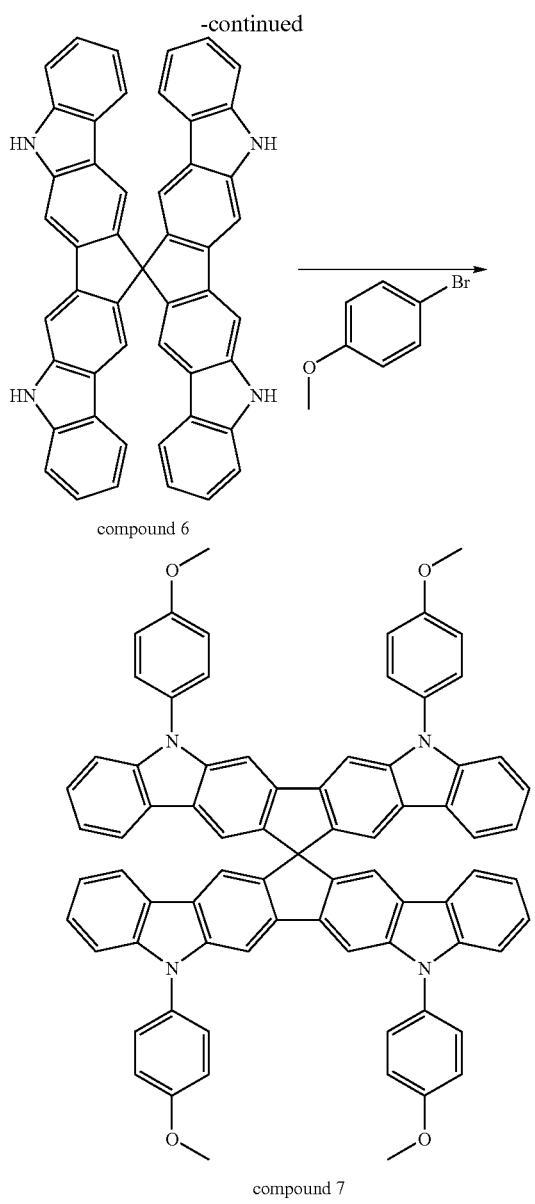

compound 6 compound 7

1) Synthesis of a Compound 1

2-bromo-biphenyl (21.55 mmol, 5 grams (g)) was dissolved in 500 milliliters (ml) of THF and then cooled to −78° C. in a nitrogen atmosphere. Subsequently, 1.6 M n-butyl lithium (14.2 ml) was slowly added thereto for 1 hour. After agitation was conducted in a nitrogen atmosphere at −78° C. for 3 hours, a solution in which 2,7-dibromo-9-fluorenone (21.55 mmol, 7.24 g) was dissolved in 50 ml of THF was slowly added thereto for 1 hour. Agitation was conducted in a nitrogen atmosphere for 20 hours and the temperature was maintained at room temperature. After the reaction, 30 ml of 1 M HCl solution was added thereto, agitation was conducted for 2 hours, and an organic layer was separated and subjected to vacuum distillation to remove THF. Purification was conducted via column chromatography using an eluent having hexane and ethyl acetate in a volume ratio of 1:1 to produce a compound 1 (18.96 mmol, 9.29 g) (Yield 88%).

2) Synthesis of a Compound 2

After the compound 1 (14.28 mmol, 7 g) was dissolved in 70 ml of acetic acid, three drops of concentrated HCl were added thereto, and refluxing was conducted for 12 hours. After the reaction, the resulting mixture was slowly dropped into 250 ml of water to produce a precipitate. After the precipitate was dried, purification was conducted using a developer having hexane and ethyl acetate in a volume ratio of 10:1 to produce a compound 2 (12.72 mmol, 6 g) (Yield 89%).

3) Synthesis of a Compound 3

The compound 2 (10.6 mmol, 5 g) was dissolved in 150 ml of chloroform and cooled to 0° C., bromine (21.19 mmol, 3.39 g) was slowly dropped thereon, and agitation was conducted for 3 hours. After the reaction, 50 ml of 2 M potassium hydroxide was injected into the reaction vessel to bring about neutralization. The reactants were then washed three times using distilled water. Next, an organic layer was separated and subjected to vacuum distillation, and the resulting solid was recrystallized using a mixed solution of chloroform and ethanol to produce a compound 3 (9.01 mmol, 5.65 g) (Yield 85%).

4) Synthesis of a Compound 4

The compound 3 (7.96 mmol, 5 g) was dissolved in 300 ml of THF and cooled to −78° C. in a nitrogen atmosphere, and 20.9 ml of 1.6 M n-butyl lithium was slowly added thereto for 1 hour. After agitation was conducted at −78° C. for 3 hours, 2-isopropoxy-4,4',5,5'-tetramethyl-1,3,2-dioxaborolane (47.76 mmol, 9.74 ml) was rapidly added thereto. Agitation was carried out in a nitrogen atmosphere for 20 hours, and the temperature was maintained at room temperature. After the reaction was completed, distilled water was added, extraction was conducted with ethyl acetate three times, and a solvent was removed using vacuum distillation to produce a compound 4 (3.6 mmol, 2.94 g) (Yield 45%).

5) Synthesis of a Compound 5

The compound 4 (3.53 mmol, 2.9 g), 1-azido-2-bromobenzene (14.16 mmol, 2.79 g), and 0.33 g of tetrakis(triphenylphosphine)palladium (Pd(PPh$_3$)$_4$) were dissolved in 40 ml of toluene and then dissolved in 20 ml of 2M Na$_2$CO$_3$, 5 ml of ethanol was added thereto, and reflux was carried out to conduct agitation for 14 hours. After the reaction was completed, distilled water was added, extraction was conducted with ethyl acetate twice, vacuum distillation was conducted to remove a solvent, and a column chromatography process was conducted to produce a compound 5 (2.26 mmol, 1.84 g) (Yield 64%)

6) Synthesis of a Compound 6

2.2 mmol (1.8 g) of compound 5 was dissolved in 70 ml of dichlorobenzene, and reflux was carried out to conduct a reaction for 3 hours. After the reaction was completed, vacuum distillation was conducted to remove a solvent, and a column chromatography process was conducted to produce a compound 6 (0.77 mmol, 0.52 g) (Yield 35%).

7) Synthesis of a Compound 7

The compound 6 (0.74 mmol, 0.5 g), 4-bromoanisole, 1.2 equivalents of sodium-t-butoxide (3.55 mmol. 0.34 g), 4 equivalents of tri-t-butyl phosphine (10 mol %), and 10 mol % of Pd$_2$(dba)$_3$ were added to 100 ml of xylene, and reflux was conducted for 3 hours. After the reaction was completed, distilled water was added, extraction was conducted twice using ethyl acetate, and vacuum distillation was conducted to remove the solvents. Finally, purification was conducted through column chromatography using a mixed solution of xylene and hexane to produce a compound 7 (0.325 g) (Yield 40%).

Figure 3:
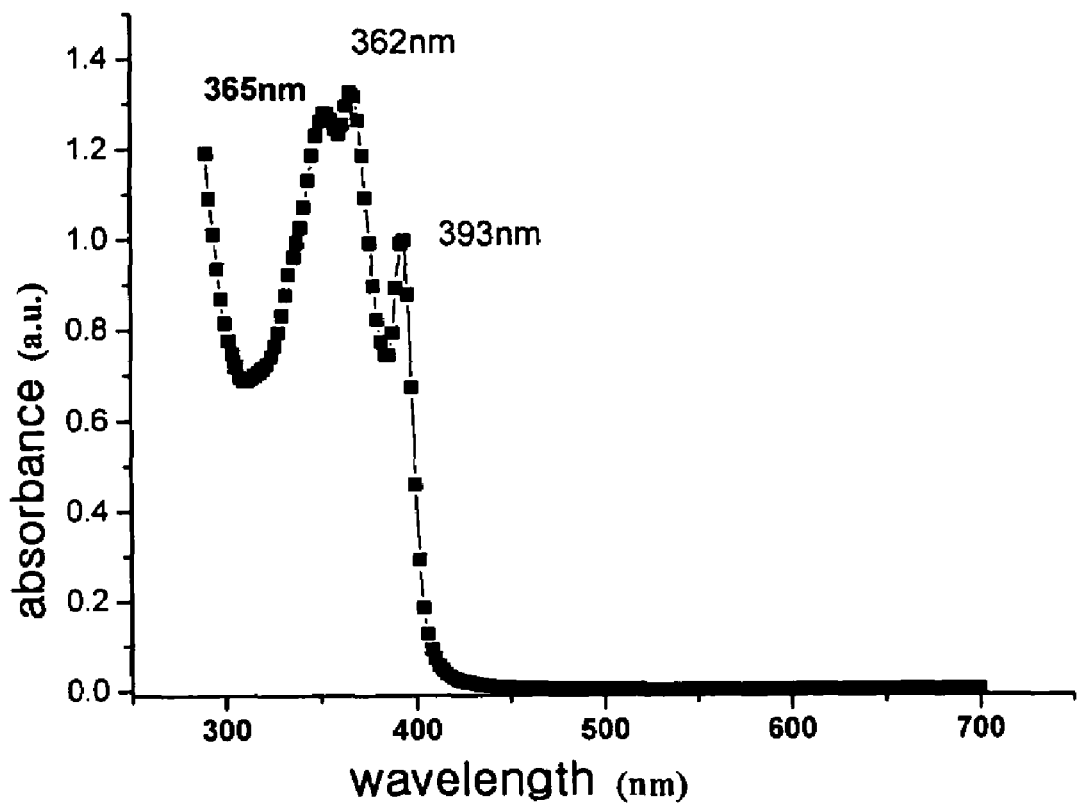
FIG. 3 illustrates an ultraviolet absorption spectrum of the material in solution according to the present invention.
Figure 4:
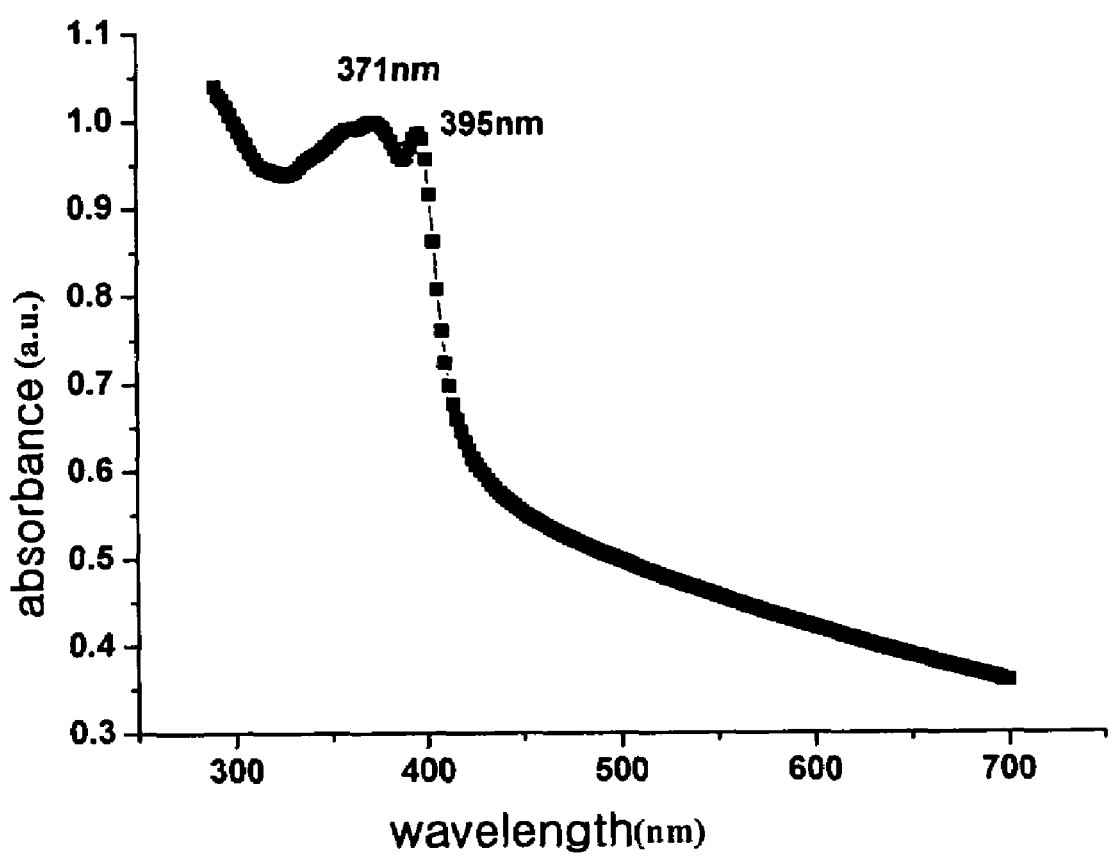
FIG. 4 illustrates an ultraviolet absorption spectrum of the material in a thin film state according to the present invention.

Ultraviolet absorption spectra of the synthesized hole transporting materials are shown in FIGS. 3 and 4. FIG. 3 illustrates the absorbance of the material present in solution, and FIG. 4 illustrates the absorbance of the material present in a film state.

Example 1

Production of a Test Device and Evaluation of Properties Thereof

After fluorine-doped tin oxide (FTO) was applied on a glass substrate using a sputter, an anatase-type $TiO_2$ particle paste having an average particle size of 13 nanometers (nm) was applied thereon using a screen printing method, and drying was conducted at 70° C. for 30 min. After the drying was completed, the resulting structure was put in an electric furnace, heated at a heating rate of 3° C./min in a normal atmosphere, and maintained at 450° C. for 30 min, and cooled at a rate that was the same as the heating rate to produce a porous $TiO_2$ film having a thickness of about 15 micrometers. Subsequently, the glass substrate on which the metal oxide layer was formed was dipped in a 0.3 millimolar (mM) ruthenium dithiocyanate 2,2'-bipyridyl-4,4'-dicarboxylate solution for 24 hours and dried to adsorb the dye on the surface of the $TiO_2$ layer. After the adsorption of the dye was completed, ethanol was sprinkled on the film to wash the un-adsorbed dye off of the metal oxide, and then dried. After the hole transporting material of the compound 7 produced in the abovementioned synthesis example was dissolved in 1 wt % chlorobenzene, the film was formed using spin coating and dried at 80° C. for 60 minutes. Next, a gold film was formed to a thickness of 30 nm using a vacuum deposition method to produce a counter electrode.

Photoelectric voltage and current of the photovoltaic device produced in the present Example were measured to calculate photoelectric conversion efficiency. In connection with this, a Xenon lamp (Oriel, 01193) was used as a light source, and solar conditions (AM 1.5) of the Xenon lamp were corrected using a standard solar cell (Fraunhofer Institute Solare Engeriessysteme, Certificate No. C-ISE369, Type of material: Mono-$Si^+$ KG filter). The photoelectric conversion efficiency of the photovoltaic device produced in the present Example was found to be 0.094% as a result of the measurement.

A material of the present invention has a structure suitable for transporting holes in view of morphology, thus an electrolyte including the hole transporting material has fair conductive properties.

Since a photovoltaic device including the material of the present invention comprises a solid electrolyte, the deterioration of properties resulting from leakage of an electrolytic solution and volatilization of the electrolytic solution is prevented, thus reliability is improved.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A novel hole transporting material shown in Formula 1:

Formula 1

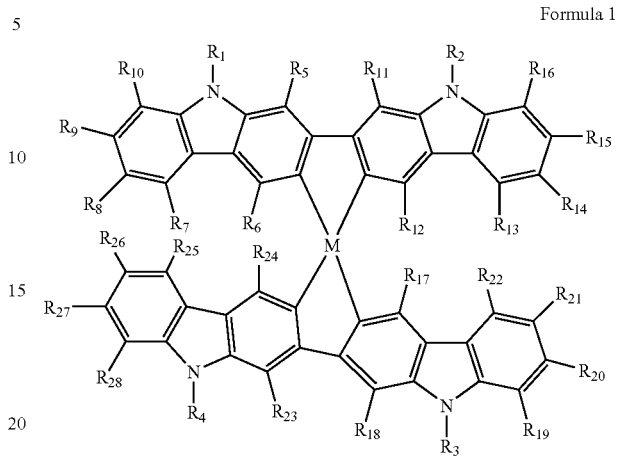

wherein $R_1$ to $R_{28}$ are the same as or different from each other, and are independently selected from a group consisting of hydrogen, a substituted or unsubstituted C1-C30 alkyl group, a substituted or unsubstituted C1-C30 alkoxy group, a substituted or unsubstituted C6-C30 aryl group, a substituted or unsubstituted C6-C30 arylalkyl group, a substituted or unsubstituted C6-C30 aryloxy group, a substituted or unsubstituted C5-C30 heteroaryl group, a substituted or unsubstituted C5-C30 heteroarylalkyl group, a substituted or unsubstituted C5-C30 heteroaryloxy group, a substituted or unsubstituted C5-C20 cycloalkyl group, and a substituted or unsubstituted C5-C30 heterocycloalkyl group, and M is C or Si.

2. The novel hole transporting material as set forth in claim 1, wherein $R_1$ and $R_2$ are different from $R_3$ and $R_4$.

3. The novel hole transporting material as set forth in claim 1, wherein $R_1$ and $R_2$, are the same as $R_3$ and $R_4$.

4. The novel hole transporting material as set forth in claim 1, wherein the hole transporting material has a structure of Formula 2

Formula 2

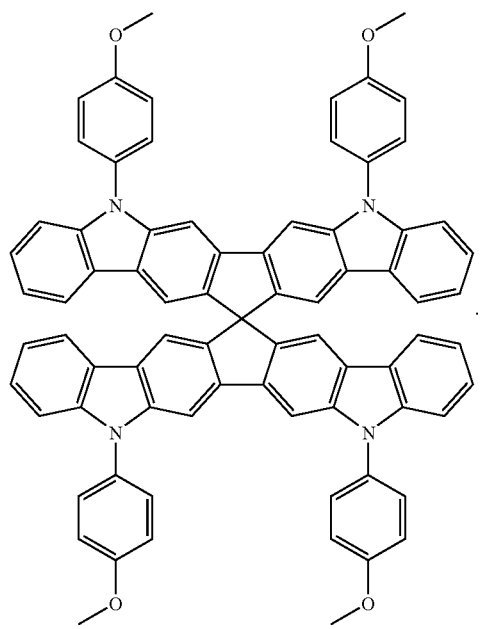

5. A solid electrolyte comprising the hole transporting material of claim 1.

6. The solid electrolyte as set forth in claim 5, further comprising a second hole transporting material selected from the group consisting of triphenylmethane, carbazole, N,N'-diphenyl'-N,N'-bis(3-methylphenyl)-1,1'biphenyl)-4,4'diamine (TPD), and 2,2',7,7'-tetrakis-(N,N-di-methoxyphenylamine)-9,9'-spirobifluorene.

7. An electronic device comprising:
   a hole transporting layer including the hole transporting material of claim 1.

8. The electronic device as set forth in claim 7, wherein the hole transporting layer further comprises a second hole transporting material selected from a group consisting of triphenylmethane, carbazole, N,N'-diphenyl'-N,N'-bis(3-methylphenyl)-1,1'biphenyl)-4,4'diamine (TPD), and 2,2',7,7'-tetrakis-(N,N-di-methoxyphenylamine)-9,9'-spirobifluorene.

9. The electronic device as set forth in claim 7, wherein the hole transporting layer is formed using spin coating, dipping, spraying, roll coating, blade coating, gravure coating, screen printing, doctor blading, electrophoresis, or a combination comprising at least one of the foregoing processes.

10. The electronic device as set forth in claim 7, wherein the electronic device is a photovoltaic device.

11. The electronic device as set forth in claim 10, wherein the photovoltaic device comprises:
   a transparent electrode in which a conductive material is applied on a substrate;
   a light absorption layer which is formed on the transparent electrode and has a dye adsorbed on a surface thereof;
   a counter electrode facing the transparent electrode; and
   a hole transporting layer interposed between the transparent electrode and the counter electrode.

12. The electronic device as set forth in claim 7, wherein the electronic device is an electroluminescent device.

* * * * *